United States Patent [19]

Sedlacek et al.

[11] 4,344,938

[45] Aug. 17, 1982

[54] AGENT FOR THE TREATMENT OF ALLERGIC REACTIONS

[75] Inventors: Hans-Herald Sedlacek; Friedrich R. Seiler, both of Marburg, Fed. Rep. of Germany

[73] Assignee: Behringwerke Aktiengesellschaft, Marburg, Fed. Rep. of Germany

[21] Appl. No.: 87,481

[22] Filed: Oct. 23, 1979

[30] Foreign Application Priority Data

Oct. 25, 1978 [DE] Fed. Rep. of Germany ....... 2846412

[51] Int. Cl.$^3$ ...................... A61K 37/00; C07G 7/00
[52] U.S. Cl. ................................ 424/177; 260/112 R; 260/112 B
[58] Field of Search ...................... 260/112 R, 112 B; 424/177

[56] References Cited

U.S. PATENT DOCUMENTS

| | | | |
|---|---|---|---|
| 4,107,298 | 8/1978 | Lüning | 260/112.5 R |
| 4,161,522 | 7/1979 | Hamburger | 424/177 |
| 4,164,495 | 8/1979 | Hansen | 260/112 B |
| 4,190,646 | 2/1980 | Goldstein | 260/112.5 R |
| 4,190,647 | 2/1980 | Goldstein | 260/112.5 R |
| 4,256,631 | 3/1981 | Yokoo et al. | 260/112 B |

OTHER PUBLICATIONS

Porter, "The Hydrolysis of Rabbit Gamma-Globulin, etc.", Biochem J. 73, 119-126 (1959).
Haupt et al., "Krystallisation etc", Klin. Wschr. 47, 270-272 (1969).
Nisonoff, "Separation of Univalent Fragments", Arch. Biochem. Biophys. 89 (2), 230(1960), [Abstract only].
Ebeling et al., "Proteinase K etc.", Eur. J. Biochem. 47, 91-97 (1974).
Davies et al., "Preparation of Antibody Fragments etc.", J. Immunol. Methods 21, 305-315 (1978).
Lin et al., "The Action of Proteolytic Enzymes etc.", J. Biol. Chem. 244, 789-793 (1969).
Sachar et al., "Photometric Method etc.", Proc. Soc. Exp. Bio. Med. 90, 323-326 (1955).
Schultze et al., "Molecular Biology of Human Proteins", Elsevier Amsterdam 1966, pp. 41-46.
Miekka et al., "Anticomplementary Activity etc.", Vox Sang. 29, 101-123 (1975).
Franklin et al., "An Unusual Protein etc.", J. Exp. Med. 105, 425-438 (1957).

*Primary Examiner*—Delbert R. Phillips
*Attorney, Agent, or Firm*—Curtis, Morris & Safford

[57] ABSTRACT

What are disclosed are a method for the prophylaxis and therapy of allergic reactions and an agent therefor, said agent containing immunoglobulins of class IgG or fragments thereof which have been immunologically modified in their Fc part.

10 Claims, No Drawings

AGENT FOR THE TREATMENT OF ALLERGIC REACTIONS

The present invention relates to an agent for the treatment of allergic reactions.

In clinical practice the term "allergic reaction" is used for hyperergic syndromes which occur as a consequence of reactions between an antigen and an antibody (reaction of the immediate type) or between an antigen and an immune cell (reaction of the delayed type) (Heilmeyer: Innere Medizin, 3rd edition; vol. 2, pages 411 to 459; published by Springer, Berlin 1971). It is a feature common to all allergic reactions of the immediate type that they are produced by an immunological fixation of an antigen to specific immunoglobulins—so-called reagins. Said reagins belong predominantly, but not exclusively, to immunoglobulins of class E (IgE). The antigen is fixed via the variable portion (Fab part) of the immunoglobulin molecule. According to the present conception of allergy, the reagin is fixed by its constant portion not fixing antigen, i.e. the Fc part, to the so-called Fc-receptors, which are present at the membrane, of certain cells (for example mast cells or basophilic granulocytes). These receptors are specific for the reagin. After addition and after immunological fixing of the specific antigen to the reagin present at the membrane, mediator substances are set free from the mast cells and basophilic granulocytes. These mediator substances set free take a substantial part in producing the syndromes in allergic reactions. Thus, for example, after contact with the specific immunoglobulin of class E and the corresponding antigen, a number of substances are set free by the basophilic granulocytes and mast cells, namely heparin, histamine, serotonin, kinin, a slow-reacting substance A, a thrombocyte-activating factor (PAP) and a factor cytophilic for eosinophilic granulocytes, which cause the clinical syndromes of allergy.

In the case of allergic reactions of the delayed type, specific antigens are fixed to immune cells, which also results in the setting-free of mediators and the development of inflammations.

The present possibilities of therapy for allergic reactions are limited: as for the symptoms, substances are administered which inhibit the action of mediators (for example, antihistamines, corticosteroids, induction of antibodies against histamine, among others) or which show an immuno-suppressive action (antilymphocyte globulin, cytostatics, corticosteroids). An approach to a causal therapy is to be seen in the so-called desensitization. It is the purpose of said desensitization to cause a tolerance of the patient to the antigen by way of a gradually increased administration of the causal antigens in each case: this tolerance may be effected by a reduced formation of specific antibodies starting the allergic reaction or by the formation of specific antibodies of a certain class which indeed fix the antigen immunologically, however, which cannot cause any allergic reactions. Another possibility lies in the administration of immunoglobulins of class IgE, which are in fact fixed to the Fc receptor of the cell involved in allergic reactions, for example the mast cell, but, which do not enter an immunological reaction with the antigen starting the disease. However, this latter therapeutical possibility has not been of any practical importance so far, as on the one hand IgE is present in human blood in traces only and can only be isolated in very small amounts, and since on the other hand the administration of the antibody may involve the transmission of allergies for other antigens with which the antibody used enters a specific reaction.

Thus, there is a demand for a causally acting therapeutic agent for allergic reactions in man. Tests which have been carried out in the field on small test animals, such as mice, rats, or preferably guinea pigs, may be applied to human beings only to a very small extent, since the allergic reactions in these test animals differ in their pathophysiology from those of humans. As it is impossible, due to infection transmission, to carry out tests on human beings, such as the Prausnitz-Kuestner test known to clinicians, experiments were performed using isolated monkey organs, since allergic reactions in monkeys are similar to those in humans, as has been well-known.

Surprisingly, it has now been found through tests of this kind that immunoglobulin of class IgG may prevent the start of an allergic reaction if its Fc part has been immunologically modified (activated). This immunological modification of the Fc part may be effected in different ways, for example by complexing, i.e. by fixing the antibody to an antigen or by fixing it to another antibody, or by an enzymatic fission of the immunoglobulin.

Thus, the invention provides an agent for the prophylaxis and therapy of allergic reactions, especially in humans or monkeys, which agent contains immunoglobulins of class IgG, or fragments thereof which have been immunologically modified in their Fc part.

As has already been known, a complexing of immunoglobulins may be effected by heating said immunoglobulins, for example, at 65° C. for 30 minutes (Franklin et al. 1957, J. Exp. Med. 105, 425), by freezing and thawing (Preudhomme et al. 1975; Ann. N.Y. Acad. Sc. 254, 254), or by a mechanical treatment, such as pipetting, stirring, treatment with ultrasonics, or circulation under pressure (Miekka et al. 1975, Vox Sang. 29, 101). Other possibilities of complexing may be envisaged by treating immunoglobulins with substances employed for precipitation and fractionation and described in detail by Schultze and Heremans (Molecular Biology of Human Proteins, pages 236 to 304, Elsevier Amsterdam 1966). For example, the treatment of immunoglobulins with neutral salts, such as sulfates, sulfites, thiosulfates, phosphates, especially ammonium sulfate, or with halides of alkali metals, ammonium or magnesium; with water-soluble organic solvents, such as ethanol or ether; with water-soluble polymers of high molecular weight, such as polyethyleneglycol, dextran, polyvinyl alcohol or polyvinyl pyrrolidone with organic cations, such as 1-ethoxy-6,9-diaminoacridine lactate (Rivanol ®); with organic or inorganic acids, such as caprylic acid, or with electric current of certain voltages. Complex-fitted immunoglobulins of this type are termed aggregates.

However, by complex-fixed immunoglobulins there are also to be understood those immunoglobulins which are fixed to an antigen immunologically in the sense of an antigen-antibody reaction.

Within the framework of the invention, fission products of IgG which contain the Fc fragment in an immunologically modified form and which were obtained by treating IgG with proteolytically-active enzymes may also be mentioned as active substances, for example fission products obtained through the fission of the immunoglobulin with papain (Porter: Biochem. J. 73, 119, 1959), plasmin, (Haupt, Heide: Klin. Wschr. 47, 270, 1969), pepsin (Porter 1959, Nisonoff et al. Arch. Biochem. Biophys. 89, 230, 1960), trypsin (Davies et al. J. Immunol. Methods 21, 305, 1978), bromelin, thermolysin, pronase (Lin et al., J. Biol. Chem. 244, 389, 1969), elastase (Sachere et al., Proc. Soc. Exp. Biol. Med. 90, 232, 1955) or proteinase K (Ebeling et al., Europ. J. Bioch. 47, 1974). The fission must not be effected to such a degree, however, that the Fc part is degraded into fission products that are inactive immunologically.

Furthermore, it has been found that fission products containing the Fc fragment of IgG activate the complement to a smaller extent than complex-fixed immunoglobulins. Since complement activation is considered a measure for the compatibility of an immunoglobulin preparation, fission products of IgG are to be regarded as being more compatible than complex-fixed IgG. The complement-activating action of complex-fixed IgG or fission products of IgG was determined by the test according to Kabat and Mayer (Experimental immunochemistry, 2nd edition; Thomas, Sprungfield). The results have been shown in Table 1.

TABLE 1

| Complement-activating action of complex-fixed IgG* or of fission products of IgG* (expressed in %) | |
|---|---|
| IgG aggregates (heated for 30 min. at 65°) | 100% |
| IgG aggregates (caprylic acid and ammonium sulfate precipitation) | 100% |
| IgG immune complexes | 100% |
| Papain Fc fragments | 30% |
| Pepsin Fc fragments (digested for 1 hour) | 15% |
| IgG, sulfonated | 0% |
| F(ab)$_2$ fragments of IgG | 0% |

*1% protein solutions each

For therapy, the preparation of the invention may be administered locally (i.e. onto the skin or mucous membranes) or systemically. In the case of systemic administration, parenteral administration (for example i.m. or s.c.) is to be preferred to oral administration. For local or parenteral administration the product of the invention is to be prepared in a formulation known to the person skilled in the art. However, for purposes of administration said product may also be mixed with serum or with serum components. In the case of oral administration, the preparation of the invention must be administered in a formulation known to the expert which prevents a digestion of the protein in the stomach and the first portion of the small intestine.

The administration of the preparation of the invention may be effected once or several times in a dosage of from 10 ng/kg of body weight (BW) to 1 g/kg of BW.

The following Examples illustrate the present invention:

EXAMPLE 1

The peritoneal cavities of monkeys (cynomolgs) under anaesthesia were opened. A certain portion of the small intestine (ileum) was taken out and immediately introduced into a nutrient solution of body temperature (known to the person skilled in the art as Tyrode's solution). Thin longitudinal strips of the intestine having a width of about 0.5 centimeter and a length of 2 cm were clamped between two hooks in Tyrode's solution maintained at body temperature, with oxygen bubbling through, in a manner that muscle contractions of the intestine portion could be registered via a recording mechanism (Schultze-Dale apparatus). Thereafter one intestinal portion was incubated with a Fc fragment of IgG obtained by papain fission (final concentration in the organ bath 35 ng/ml), and another intestinal portion was incubated for the purpose of control with a physiological NaCl solution or with albumin, or with Fab$_2$ fragments of IgG prepared according to Reid (Immunology 20, 649, 1971) in a corresponding final concentration, for about 30 minutes at 37° C. Subsequently, reagin-containing patient serum, to which the allergy-causing antigen had been added, was introduced into each mixture in amounts of 0.2 ml and 0.5 ml for 30 ml of organ bath solution. In the case of the untreated intestine, the introduction of the mixture of serum and antigen results in allergic reactions, i.e. an increase in tonus and frequency of the intestinal mobility. As may be seen from Table 2, the previous incubation with papain Fc, however, has an inhibitory effect on the allergic reaction produced by the mixture of reagin-containing patient serum and allergy-causing antigen.

TABLE 2

Inhibition of the allergic reaction in monkey intestines by Fc fragments of IgG
Reagin: Serum of patients allergic to Schistosoma antigen

| Pre-incubation of the intestine with | Increase in intestine tonus and contraction frequency (in %) (as compared with 3 µg of histamine/ml = 100%) | | Inhibition of the allergic reaction (in %) | |
|---|---|---|---|---|
| | 7 µl/ml* | 17 µl/ml* | 7 µl/ml* | 17 µl/ml* |
| — | 18 | 30 | — | — |
| papain-Fc fragments | 0 | 20 | 100 | 33 |

*allergic reaction caused by the addition of 7 µl and 17 µl/ml, respectively, of a mixture of the serum of allergic persons and Schistosoma antigen (v:v = 1:1)

EXAMPLE 2

Longitudinal strips of monkey intestines, which were obtained as described in Example 1, are incubated with Fc fragments of IgG obtained in different ways (papain-Fc, pepsin-Fc split for 1 hour) as well as with IgG complex-fixed, i.e. aggregated, according to different methods (heating, caprylic acid precipitation or ammonium sulfate precipitation), and for the purpose of control with F(ab)$_2$ fragments of IgG, or with chemically modified papain-Fc (Fc chemically modified via a diazotization according to U.S. Pat. No. 3,873,697), in a final concentration of 500 µg/ml of Tyrode's solution for 15 minutes at 37° C. Subsequently the organ pieces are withdrawn and are incubated at 37° C. in Tyrode's solution containing 50 µl/ml of patient serum. After 15 minutes the organ strips are suspended in the Schultz-Dale apparatus, as has been mentioned in Example 1, and 0.5 ml of cow hair suspension (20 mg of cow hair cut into pieces and suspended in 10 ml of Tyrode's solution) is added to the organ bath (30 ml). The results are given in Table 3. They show clearly a complete inhibition of the allergic reaction by immunologically modified Fc, i.e. by complex-fixed (aggregated) IgG and by Fc obtained through papain fission, and a substantially reduced allergic reaction by Fc obtained through plasmin or pepsin fission. However, there is no inhibition by F(ab)$_2$ fragments of IgG or by chemically modified Fc.

TABLE 3

Inhibition of the allergic reaction in monkey intestines by Fc fragments or aggregates (test preparations) of IgG
Reagin: Serum of a patient allergic to cow hair and (less) mouse hair

| Pre-incubation of the intestine with (test substances) | Allergen* | Increase in intestine tonus and contraction frequency (in %) (as compared with 3 μg of histamine/ml = 100%) | Inhibition of the allergic reaction |
|---|---|---|---|
| — | cow hair | 36 | |
| — | mouse hair | 20 | |
| — | rat hair | 0 | |
| F(ab)2 fragments | cow hair | 37 | 0 |
| aggregates (heated for 10 min. at 56°) | " | 0 | 100 |
| papain-Fc fragments | " | 0 | 100 |
| plasmin-Fc fragments | " | 18 | 50 |
| pepsin-Fc fragments digested for 1 hour | " | 18 | 50 |
| chem. treated papain-Fc fragments | " | 37.5 | —0 |
| IgG aggregates (heated at 65° C./30 min) | " | 0 | 100 |
| IgG (aggregate portion 20%) (caprylic acid and ammonium sulfate precipitation) | " | 0 | 100 |
| IgG (aggregate portion 10%) (caprylic acid and ammonium sulfate precipitation | " | 6 | 84 |

*Addition of the allergen after pre-incubation of the intestine with test substances and with the serum of allergic persons (17 μl/ml)

EXAMPLE 3 (PATIENT ALLERGIC TO RABBIT HAIR)

The experiment is started as in Example 2: Incubation of the longitudinal strips of monkey intestines with different Fc fragments of IgG (papain-Fc, plasmin-Fc, pepsin-Fc after 1 hour of digestion) or with IgG complex-fixed in different ways (antigen immune complexes in the antigen and in the antibody excess, IgG subjected to a thermal treatment, IgG treated with caprylic acid and ammonium sulfate according to Schultze, Heremans 1966) is carried out. For purposes of control, incubation was effected with F(ab)2 fragments of IgG whose Fc part was chemically modified (sulfonation according to Schultze and Heremans, Molecular Biology of Human proteins, page 43, Elsevier Amsterdam 1966) and with IgG freed from aggregates by ultracentrifugation (2 hours at 120,000 g).

Subsequently incubation with the patient serum is performed, whereupon the organ is suspended in the Schultz-Dale apparatus and a suspension of rabbit hair is added.

Results show a complete inhibition of the allergic reaction by complex-fixed IgG and Fc obtained through papain, plasmin and pepsin fission, but no inhibition by F(ab)2 fragments of IgG, by IgG chemically modified in the Fc part and by aggregate-free IgG.

EXAMPLE 4 (PATIENT ALLERGIC TO POLLEN)

Patient H.S. with pronounced pollen allergy present for 5 years. At the onset of the disease due to the seasonal dissemination of pollen, 0.5 ml of papain-Fc is applied intranasally while being distributed to both nostrils (10 mg/ml of physiological NaCl solution). This treatment is repeated four times in intervals of 2 weeks.
Result:

Strong reduction of sneezing and nasal secretion up to the elimination of symptoms.

What is claimed is:

1. A pharmaceutical preparation for the prophylaxis or therapy of allergic reactions, said preparation comprising complex-fixed IgG immunoglobulin modified in the Fc-portion thereof by aggregation or immunological fixing to an antigen, or comprising immunologically active fragments of IgG immunoglobulin obtained by proteolytic fission of IgG immunoglobulin, said fragments being modified in the Fc-portion thereof, together with a pharmaceutically-acceptable carrier therefor.

2. A pharmaceutical preparation as in claim 1 comprising complex-fixed IgG immunoglobulin wherein said complex-fixed IgG immunoglobulin is aggregated.

3. A pharmaceutical preparation as in claim 1 comprising complex-fixed IgG immunoglobulin wherein said complex-fixed IgG immunoglobulin is immunologically fixed to an antigen.

4. A pharmaceutical preparation as in claim 1 comprising immunologically active fragments of IgG immunoglobulin.

5. A pharmaceutical preparation as in claim 4 wherein said immunologically active fragments are obtained by proteolytic fission of IgG immunoglobulin with an enzyme selected from the group consisting of papain, plasmin, pepsin, and trypsin.

6. A method for the prophylaxis or therapy of allergic reactions in a patient susceptible to or suffering therefrom, which method comprises locally, orally, or parenterally administering to said patient an anti-allergically effective amount of a complex-fixed IgG immunoglobulin modified in the Fc-portion thereof by aggregation or immunological fixing to an antigen, or of immunologically active fragments of IgG immunoglobulin obtained by proteolytic fission of IgG immunoglobulin, said fragments being modified in the Fc-portion thereof.

7. A method as in claim 6 wherein complex-fixed IgG immunoglobulin is administered, the Fc-portion of which has been modified by aggregation.

8. A method as in claim 6 wherein complex-fixed IgG immunoglobulin is administered, the Fc-portion of which has been modified by fixing to an antigen.

9. A method as in claim 6 wherein immunologically active fragments of IgG immunoglobulin are administered.

10. A method as in claim 6 wherein said immunologically active fragments of IgG immunoglobulin are obtained by proteolytic fission of IgG immunoglobulin with an enzyme selected from the group consisting of papain, plasma, pepsin, and trypsin.

* * * * *